(12) United States Patent
Hawes et al.

(10) Patent No.: US 12,053,020 B2
(45) Date of Patent: Aug. 6, 2024

(54) E-VAPOR DEVICES INCLUDING PRE-SEALED CARTRIDGES

(71) Applicant: Altria Client Services LLC, Richmond, VA (US)

(72) Inventors: Eric Hawes, Richmond, VA (US); Raymond Lau, Richmond, VA (US); Ben Sharp, Cambridge (GB)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/875,157

(22) Filed: May 15, 2020

(65) Prior Publication Data

US 2020/0275694 A1   Sep. 3, 2020

Related U.S. Application Data

(60) Division of application No. 15/239,304, filed on Aug. 17, 2016, now Pat. No. 10,653,181, which is a
(Continued)

(51) Int. Cl.
*A24F 40/30*      (2020.01)
*A24F 40/40*      (2020.01)
(Continued)

(52) U.S. Cl.
CPC .............. *A24F 40/30* (2020.01); *A24F 40/40* (2020.01); *A24F 40/42* (2020.01); *A24F 40/46* (2020.01);
(Continued)

(58) Field of Classification Search
CPC ............................. A24F 40/42; A61M 15/005
See application file for complete search history.

(56) References Cited

U.S. PATENT DOCUMENTS 5,269,327 A   12/1993  Counts et al.
5,819,756 A * 10/1998  Mielordt ............... A24F 47/008
                                                131/330
(Continued)

FOREIGN PATENT DOCUMENTS

CA     2866283 A1   12/2014
CN   101986906 A    3/2011
(Continued)

OTHER PUBLICATIONS

International Search Report and Written Opinion mailed Aug. 18, 2016for corresponding International Application No. PCT/US2016/028039.
(Continued)

*Primary Examiner* — Philip Y Louie
*Assistant Examiner* — Sonny V Nguyen

(57) ABSTRACT

An e-vapor device may include a cartridge configured to hold a pre-vapor formulation therein. The e-vapor device may additionally include a dispensing body including a ratchet assembly and configured to receive a vaporizer to interact with the ratchet assembly. The vaporizer is configured to access the pre-vapor formulation in the cartridge via a coupling action and to heat the pre-vapor formulation to generate a vapor. The ratchet assembly is configured to undergo a mechanical incrementation with each coupling action to facilitate a simultaneous removal of the cartridge with the vaporizer coupled thereto after a designated number of coupling actions. Accordingly, the overuse of the vaporizer and the adverse sensory effects associated therewith can be reduced or prevented.

9 Claims, 23 Drawing Sheets

Related U.S. Application Data continuation-in-part of application No. 14/998,040, filed on Apr. 22, 2015, now Pat. No. 10,602,774.

(51) Int. Cl.

| *A24F 40/42* | (2020.01) |
|---|---|
| *A24F 40/46* | (2020.01) |
| *A24F 40/485* | (2020.01) |
| *A61M 11/04* | (2006.01) |
| *A61M 15/06* | (2006.01) |
| *A24F 40/10* | (2020.01) |

(52) U.S. Cl.
CPC ......... *A24F 40/485* (2020.01); *A61M 11/041* (2013.01); *A61M 11/042* (2014.02); *A61M 15/06* (2013.01); *A24F 40/10* (2020.01)

(56) References Cited

U.S. PATENT DOCUMENTS

| 6,053,176 | A * | 4/2000 | Adams ................ A24F 47/008 128/202.21 |
|---|---|---|---|
| 8,757,169 | B2 | 6/2014 | Gysland |
| 8,851,068 | B2 | 10/2014 | Cohen et al. |
| 2002/0078951 | A1 * | 6/2002 | Nichols ............ A61M 15/0045 128/200.22 |
| 2002/0078955 | A1 | 6/2002 | Nichols et al. |
| 2009/0151717 | A1 | 6/2009 | Bowen et al. |
| 2009/0178676 | A1 * | 7/2009 | Villax ............... A61M 15/0045 128/203.15 |
| 2011/0094523 | A1 * | 4/2011 | Thorens ............... H05B 3/0014 131/194 |
| 2011/0271958 | A1 * | 11/2011 | Sawant ............ A61M 15/0075 128/203.21 |
| 2013/0037041 | A1 | 2/2013 | Worm et al. |
| 2013/0068239 | A1 | 3/2013 | Youn |
| 2013/0081642 | A1 | 4/2013 | Safari |
| 2013/0152922 | A1 | 6/2013 | Benassayag et al. |
| 2013/0167854 | A1 | 7/2013 | Shin |
| 2013/0199528 | A1 | 8/2013 | Goodman et al. |
| 2013/0298905 | A1 | 11/2013 | Levin et al. |
| 2014/0041658 | A1 | 2/2014 | Goodman et al. |
| 2014/0096782 | A1 | 4/2014 | Ampolini et al. |
| 2014/0109921 | A1 | 4/2014 | Chen |
| 2014/0158129 | A1 | 6/2014 | Pratt, Jr. et al. |
| 2014/0224248 | A1 | 8/2014 | Edwards et al. |
| 2014/0253144 | A1 | 9/2014 | Novak, III et al. |
| 2014/0270727 | A1 | 9/2014 | Ampolini et al. |
| 2014/0283859 | A1 | 9/2014 | Minskoff et al. |
| 2014/0301721 | A1 | 10/2014 | Ruscio et al. |
| 2015/0040929 | A1 | 2/2015 | Hon |
| 2015/0090253 | A1 * | 4/2015 | Farrow ............. A61M 15/0003 128/200.14 |
| 2015/0208729 | A1 * | 7/2015 | Monsees ............... H02J 7/0044 131/329 |
| 2015/0313288 | A1 * | 11/2015 | Liu ..................... A24F 40/49 131/329 |
| 2015/0328415 | A1 * | 11/2015 | Minskoff ................ A24F 40/60 128/202.21 |
| 2016/0095356 | A1 * | 4/2016 | Chan ..................... A24F 40/30 392/390 |
| 2016/0128384 | A1 * | 5/2016 | Luciani ................ A24F 47/008 131/329 |
| 2016/0135504 | A1 | 5/2016 | Li et al. |
| 2016/0219934 | A1 | 8/2016 | Li et al. |
| 2016/0270441 | A1 | 9/2016 | Lewis et al. |
| 2016/0324214 | A1 * | 11/2016 | Brunner ................ A24F 40/30 |
| 2016/0345636 | A1 * | 12/2016 | Liu ...................... H05B 1/0227 |
| 2017/0006917 | A1 | 1/2017 | Alvarez |
| 2017/0086498 | A1 | 3/2017 | Daryani |
| 2017/0150753 | A1 | 6/2017 | Macko |
| 2017/0156403 | A1 * | 6/2017 | Gill ....................... H05B 6/108 |
| 2017/0246405 | A1 * | 8/2017 | Wensley .............. A61M 11/001 |
| 2018/0098570 | A1 | 4/2018 | Hon |
| 2018/0104214 | A1 | 4/2018 | Raichman |
| 2018/0206551 | A1 | 7/2018 | Liu |

FOREIGN PATENT DOCUMENTS

| CN | 102892448 | A | 1/2013 | |
|---|---|---|---|---|
| CN | 103501847 | A | 1/2014 | |
| CN | 103929988 | A | 7/2014 | |
| CN | 104114050 | A | 10/2014 | |
| CN | 204104838 | U | 1/2015 | |
| CN | 204120222 | U | 1/2015 | |
| EP | 2617303 | A1 | 7/2013 | |
| WO | WO-2012026963 | A2 * | 3/2012 | ........ A61M 16/1065 |
| WO | WO-2013/040193 | A2 | 3/2013 | |
| WO | WO-2014/195859 | A2 | 12/2014 | |
| WO | WO-2014/207719 | A1 | 12/2014 | |

OTHER PUBLICATIONS

International Search Report and Written Opinion for Corresponding Application No. PCT/US2016/028039 dated Nov. 2, 2017.
Eurasian Notification dated Nov. 9, 2018 for corresponding Eurasian Application No. 201792326.
Office Action for corresponding U.S. Appl. No. 15/239,304 dated Feb. 26, 2019.
Office Action for corresponding U.S. Appl. No. 14/998,040 dated Apr. 3, 2019.
Office Action for corresponding U.S. Appl. No. 15/239,304 dated Aug. 21, 2019.
Office Action for corresponding U.S. Appl. No. 14/998,040 dated Aug. 22, 2019.
Notice of Allowance for U.S. Appl. No. 14/998,040 dated Oct. 2, 2019.
Office Action for corresponding Chinese Application No. 201680023593.0 dated Nov. 4, 2019.
Office Action for corresponding U.S. Appl. No. 15/239,304 dated Nov. 1, 2019.
U.S. Notice of Allowance dated Dec. 3, 2019 for corresponding U.S. Appl. No. 14/998,040.
Notice of Allowance for U.S. Appl. No. 15/239,304 dated Jan. 29, 2020.
Office Action for Chinese Application No. 201680023593.0 dated Sep. 2, 2020 and English translation.
Substantive Examination Adverse Report for Malaysian Patent Application No. PI 2017001553 dated Mar. 24, 2021.
First Office Action for Israel patent application No. 254729 dated May 31, 2021, three pages.
Office Action for Israel Application No. 294323 dated Jul. 26, 2023.
Office Action for Chinese Patent Application No. 202110167728.3, dated Dec. 4, 2023, including English translation.
Office Action for Chinese Patent Application No. 202110167728, dated May 23, 2024, including English translation.

\* cited by examiner

100

104

102

106

112

112a

112b

E-VAPOR DEVICES INCLUDING PRE-SEALED CARTRIDGES

CROSS-REFERENCE TO RELATED APPLICATIONS

The present application is a divisional under 35 U.S.C. § 121 of U.S. application Ser. No. 15/239,304, filed Aug. 17, 2016, which is a continuation-in-part under 35 U.S.C. § 120 of U.S. application Ser. No. 14/998,040 (converted to non-provisional from U.S. Provisional Application No. 62/151,248), filed Apr. 22, 2015, the entire contents of each of which are hereby incorporated herein by reference.

BACKGROUND

Field

The present disclosure relates to electronic vapor devices including self-contained articles including pre-vapor formulations.

Description of Related Art

Some e-vapor devices include a first section coupled to a second section via a threaded connection. The first section may be a replaceable cartridge, and the second section may be a reusable fixture. The threaded connection may be a combination of a male threaded member on the first section and a female threaded receiver on the second section. The first section includes an outer tube (or housing) extending in a longitudinal direction and an inner tube within the outer tube. The inner tube may be coaxially positioned within the outer tube. The second section may also include the outer tube (or housing) extending in a longitudinal direction. The e-vapor device includes a central air passage defined in part by the inner tube and an upstream seal. Additionally, the e-vapor device includes a reservoir. The reservoir is configured to hold a pre-vapor formulation and optionally a storage medium operable to store the pre-vapor formulation therein. The reservoir is contained in an outer annulus between the outer tube and the inner tube. The outer annulus is sealed by the seal at an upstream end and by a stopper at a downstream end so as to prevent leakage of the pre-vapor formulation from the reservoir.

SUMMARY

An e-vapor device may include a cartridge configured to hold a pre-vapor formulation therein. The e-vapor device may additionally include a dispensing body including a ratchet assembly and configured to receive a vaporizer to interact with the ratchet assembly. The vaporizer is configured to access the pre-vapor formulation in the cartridge via a coupling action and to heat the pre-vapor formulation to generate a vapor. The ratchet assembly is configured to undergo a mechanical incrementation with each coupling action to facilitate a simultaneous removal of the cartridge with the vaporizer coupled thereto after a designated number of coupling actions.

The cartridge may be in a form of a mouthpiece. The cartridge may be a hermetically-sealed container. The cartridge may be sealed with a ball check valve arrangement.

The vaporizer may be configured to press against a ball structure of the ball check valve arrangement to release the pre-vapor formulation within the cartridge during the coupling action. The vaporizer may be configured to unite with the cartridge via a snap-fit arrangement during the coupling action.

The ratchet assembly may be configured to rotate in response to the coupling action as part of the mechanical incrementation. The ratchet assembly may be configured to initially latch onto the vaporizer during the coupling action and to incrementally disengage from the vaporizer with each coupling action such that the vaporizer is released from the ratchet assembly after the designated number of coupling actions. Alternatively, the ratchet assembly may be configured to incrementally engage the vaporizer to the cartridge with each coupling action such that the vaporizer is conjoined to the cartridge after the designated number of coupling actions. The ratchet assembly may be configured to facilitate the simultaneous removal of the cartridge with the vaporizer coupled thereto after two to ten coupling actions (e.g., three to six coupling actions).

The e-vapor device may further include a mouthpiece structure configured to house the cartridge and to connect with the dispensing body such that the cartridge is between the mouthpiece structure and the dispensing body. An outer surface of the cartridge may be configured to conform to an inner surface of the mouthpiece structure. The cartridge may be integrated with the mouthpiece structure.

An e-vapor device may include a cartridge configured to hold a pre-vapor formulation therein, the cartridge being a sealed container. The e-vapor device may additionally include a dispensing body including a mouthpiece end and a vaporizer at an opposing base end. The base end is configured to couple with the cartridge such that the pre-vapor formulation is in fluidic communication with the vaporizer. The vaporizer is configured to heat the pre-vapor formulation to generate a vapor.

The cartridge may be sealed with a ball check valve arrangement. The dispensing body may further include a battery between the mouthpiece end and the vaporizer.

An e-vapor device may include a cartridge including a plurality of compartments, each of the plurality of compartments configured to hold a pre-vapor formulation therein. The e-vapor device may additionally include a dispensing body including a vaporizer. The cartridge may be rotatably-mounted on the dispensing body via the vaporizer. The cartridge is configured to rotate around the vaporizer such that one of the plurality of compartments is aligned so as to be in fluidic communication with the vaporizer.

The cartridge may be disk-shaped. The plurality of compartments are fluidically-isolated from each other. The vaporizer may be configured to remain stationary during a rotation of the cartridge.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
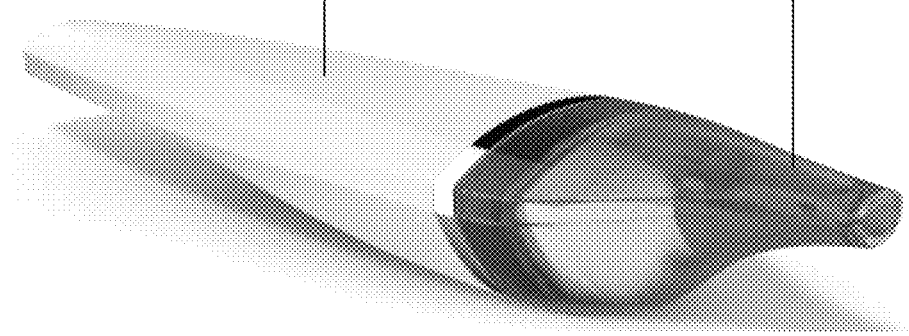
FIG. 1 is a perspective view of an e-vapor device with a mouthpiece/cartridge configuration according to an example embodiment.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a perspective view of an e-vapor device with a mouthpiece/cartridge configuration according to an example embodiment. Referring to FIG. 1, an e-vapor device 100 includes a mouthpiece structure 102 that is removably connected to a dispensing body 104. The mouthpiece structure 102 and the dispensing body 104 are shaped so as to provide a relatively smooth transition between their respective surfaces when joined together to form the e-vapor device 100. In an example embodiment, the e-vapor device 100 may have a flattened form so as to be wider than it is tall. Additionally, the dispensing body 104 may constitute a majority of the length of the e-vapor device 100. The back of the e-vapor device 100 (e.g., upper surface shown in FIG. 1) may be flatter than the underside of the e-vapor device 100. For instance, the underside of the e-vapor device 100 may have a belly that is fuller (e.g. more extended) at the adjoining portions of the mouthpiece structure 102 and the dispensing body 104 than at the end portions of the e-vapor device 100.

The mouthpiece structure 102 may include a cartridge that is configured to hold a pre-vapor formulation (e.g., e-liquid) therein. A pre-vapor formulation is a material or combination of materials that may be transformed into a vapor. For example, the pre-vapor formulation may be a liquid, solid, and/or gel formulation including, but not limited to, water, beads, solvents, active ingredients, ethanol, plant extracts, natural or artificial flavors, and/or vapor formers such as glycerine and propylene glycol. The cartridge may be a hermetically-sealed container. The cartridge will be discussed in further detail in connection with subsequent figures. The vapor generated is drawn out of the e-vapor device 100 via the proximal end of the mouthpiece structure 102 (which is opposite to the end that is connected to the dispensing body 104). The mouthpiece structure 102 may taper toward the proximal end to form a snout-like configuration, which defines an outlet for the vapor. The dispensing body 104 may also taper toward the distal end (which is opposite to the end that is connected to the mouthpiece structure 102) to form a flattened tail-like structure. However, it should be understood that the mouthpiece structure 102, the dispensing body 104, and the overall e-vapor device 100 are not limited to the above examples and, thus, may have other suitable shapes, configurations, and forms (e.g., symmetrical shape).

The mouthpiece structure 102 may be integrated with the cartridge so as to engage with (and disengage from) the dispensing body 104 as a combined structure. In such an instance, the cartridge will not separate from the mouthpiece structure 102 during a normal operation of the e-vapor device 100. As a result, detaching the mouthpiece structure 102 from the dispensing body 104 will also result in the removal of the cartridge. Consequently, the mouthpiece structure 102 may be a single-use structure that is discarded with the cartridge (e.g., when replacing the cartridge).

Additionally, rather than a combined structure, the cartridge itself may be in a form of the mouthpiece structure 102 so as to be a single structure (instead of a plurality of integrated elements) that is configured to be attached/detached from the dispensing body 104. The cartridge may be the mouthpiece structure 102, and the mouthpiece structure 102 may be the cartridge (instead of integrating an element that will function as the mouthpiece structure 102 with another element that will function as the cartridge to form a combined structure). In such an example, the internal volume of the mouthpiece structure 102 (other than the vapor passage extending therethrough) may contain the pre-vapor formulation.

Alternatively, the mouthpiece structure 102 may be an independent element that houses the cartridge such that the cartridge may be separated from the mouthpiece structure 102 during a normal operation of the e-vapor device. For example, the cartridge may be configured to initially connect to the dispensing body 104 prior to connecting the mouthpiece structure 102 to the dispensing body 104 (and/or to the cartridge). The removal of the mouthpiece structure 102 and the cartridge may occur in the reverse order of their connection to the dispensing body 104. For instance, to replace the cartridge of the e-vapor device 100, the mouthpiece structure 102 may be initially detached from the dispensing body 104 to expose the cartridge, and then the cartridge may be detached from the dispensing body 104. After connecting the replacement cartridge to the dispensing body 104, the mouthpiece structure 102 may be reconnected to the dispensing body 104 so as to cover the cartridge.

Because the mouthpiece structure 102 may be configured as a permanent or semi-permanent element of the e-vapor device 100 and, thus, does not need to be discarded each time the cartridge is replaced, the mouthpiece structure 102 may be provided with aesthetic effects. Notably, the mouthpiece structure 102 may, in addition to its intended functionality, provide a visual or other sensory appeal to the adult vaper. In particular, the mouthpiece structure 102 may be formed of an ornamental material (e.g., wood, metal, ceramic, plastic) and/or include designs (e.g., patterns, images, characters). Thus, the mouthpiece structure 102 may be customized so as to provide an expression of personality and individuality by an adult vaper.

The dispensing body 104 may include a ratchet assembly and is configured to receive a vaporizer to interact with the ratchet assembly. The ratchet assembly will be discussed in further detail in connection with subsequent figures. The vaporizer is configured to access the pre-vapor formulation in the cartridge via a coupling action and to heat the pre-vapor formulation to generate a vapor. In an example embodiment, the ratchet assembly is configured to undergo a mechanical incrementation with each coupling action (between the vaporizer and the cartridge) to facilitate a simultaneous removal of the cartridge with the vaporizer coupled thereto after a designated number of coupling actions. As a result, the potential for overuse of the vaporizer (and the adverse sensory effects stemming therefrom) can be reduced or prevented.

Figure 2:
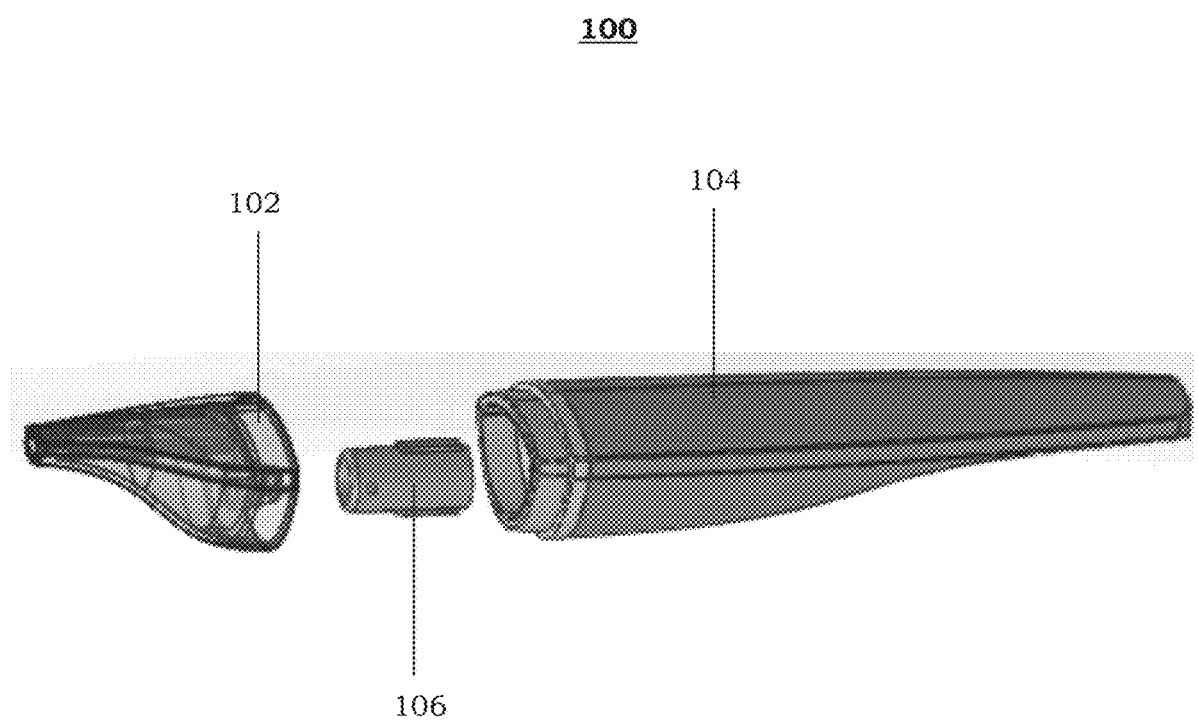
FIG. 2 is a partially exploded view of the e-vapor device in FIG. 1.

FIG. 2 is a partially exploded view of the e-vapor device in FIG. 1. Referring to FIG. 2, the dispensing body 104 is configured to receive a vaporizer 106. The vaporizer 106 may be cylindrically shaped with one or more guide structures on its outer side wall. The one or more guide structures may be in the form of one or more parallel ridges that extend along a partial length of the vaporizer 106. For instance, the ridges may be in the form of two parallel strips on opposite sides of the vaporizer 106, wherein the strips extend longitudinally from an end of the vaporizer 106 (that will be received by the dispensing body 104) along a partial length of the vaporizer 106 (e.g., along one-third to two-thirds a length of the vaporizer 106), although example embodiments are not limited thereto. When assembled, the mouthpiece structure 102 is configured to engage the concave end of the vaporizer 106 as well as the dispensing body 104.

Figure 3:
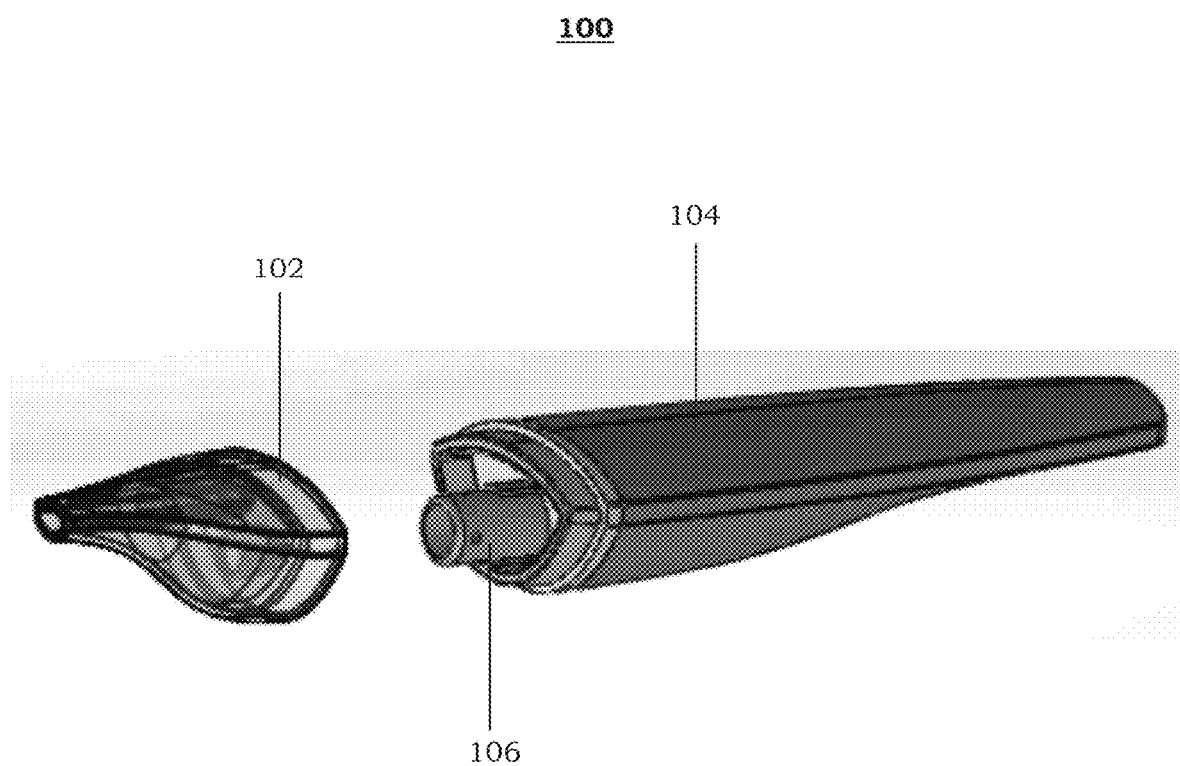
FIG. 3 is another partially exploded view of the e-vapor device in FIG. 1.

FIG. 3 is another partially exploded view of the e-vapor device in FIG. 1. Referring to FIG. 3, the dispensing body 104 includes a recess configured to accommodate the cylindrical shape of the vaporizer 106 and the guide structures on the outer side wall thereof so as to interact with a ratchet assembly within the dispensing body 104. The depth of the recess is such that the vaporizer 106 protrudes therefrom when in a neutral, resting position in the recess. In an example embodiment, the guide structures on the outer side wall of the vaporizer 106 also protrude from the recess when the vaporizer 106 is at equilibrium therein (e.g., in the absence of an external force pushing the vaporizer 106 into the recess). Because at least the surface defining the opening to the recess may be contoured to correspond to the circular cross-section of the vaporizer 106 and the guide structures on the outer side wall thereof, the vaporizer 106 may remain aligned in the recess and, thus, prevented from rotating therein while the guide structures overlap with the surface defining the opening to the recess. On the other hand, below the surface defining the opening to the recess, the volume of the recess may have a cylindrical shape that is larger than the cylindrical shape of the vaporizer 106 in order to accommodate the guide structures on the outer side wall thereof. As a result, the vaporizer 106 will be able to rotate if the vaporizer 106 is pushed into the dispensing body 104 such that the guide structures no longer overlap with the surface defining the opening to the recess.

Alternatively, the volume of the recess (in addition to the surface defining the opening thereto) may also correspond to the cylindrical shape of the vaporizer 106 and the guide structures on the outer side wall thereof such that the vaporizer 106 will remained aligned and, thus, unable to rotate while in the recess (regardless of whether an external force is applied to push vaporizer 106 into the dispensing body 104 such that the guide structures are below the surface defining the opening to the recess). However, it should be understood that example embodiments are not limited to the above, and other suitable configurations are possible depending on the intended interaction between the vaporizer 106 and the dispensing body 104 and/or the ratchet assembly (which will be discussed in further detail below).

Figure 4:
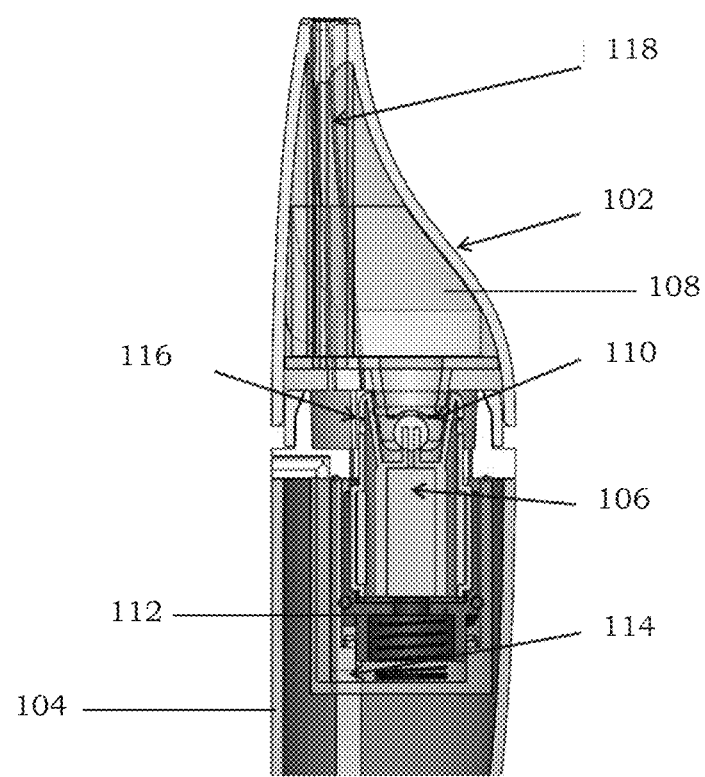
FIG. 4 is a partial, cross-sectional view of the e-vapor device in FIG. 1.

FIG. 4 is a partial, cross-sectional view of the e-vapor device in FIG. 1. Referring to FIG. 4, the mouthpiece structure 102 is configured to house the cartridge 108 and to connect with the dispensing body 104 such that the cartridge 108 is between the mouthpiece structure 102 and the dispensing body 104. An outer surface of the cartridge 108 may be configured to conform to an inner surface of the mouthpiece structure 102. The mouthpiece structure 102 and the cartridge 108 may be configured as two independent elements that are designed to be separated during a normal operation of the e-vapor device 100. In such an instance, the mouthpiece structure 102 may be reusable, while the cartridge 108 may be disposable.

Alternatively, the mouthpiece structure 102 and the cartridge 108 may be integrated so as to form a single, combined structure that is not designed to be separated during a normal operation of the e-vapor device 100. In such an instance, the combined mouthpiece structure 102 and cartridge 108 may be disposable. Furthermore, the cartridge 108 itself may be in the form of the mouthpiece structure 102 (and vice versa) such that an internal volume therein (other than the vapor passage 118) may be filled with the pre-vapor formulation.

The cartridge 108 may connect with the vaporizer 106 via a number of possible configurations. Additionally, the mouthpiece structure 102 may engage with the dispensing body 104 to fortify the connection between the cartridge 108 and the vaporizer 106. Suitable attachment structures that may be provided on the applicable surfaces of the e-vapor device 100 to be joined include mating member/recess type arrangements and magnetic arrangements, although example embodiments are not limited thereto.

For instance, the attachment structure may include a mating member that is formed on a first surface of the e-vapor device 100 and a corresponding recess that is formed on a second surface of the e-vapor device 100. In a non-limiting embodiment, the mating member may be a rounded structure to facilitate the engagement/disengagement of the attachment structure, while the recess may be a concave indentation that corresponds to the curvature of the rounded structure. The mating member may also be spring-loaded so as to retract (via spring compression) during an initial insertion and to protract (via spring decompression) when mating member becomes aligned with the corresponding recess. The engagement of the mating member with the corresponding recess may result in an audible click, which notifies the adult vaper of a proper connection.

In another example, the attachment structure may include a magnetic arrangement. For instance, a first magnet may be arranged in a first surface of the e-vapor device 100 and a second magnet may be arranged in a second surface of the e-vapor device 100. The first and/or second magnets may be exposed or hidden from view behind a layer of material. The first and second magnets are oriented so as to be attracted to each other, and a plurality of pairs of the first and second magnets may be provided to ensure a proper connection between the desired surfaces.

In an example embodiment, the cartridge 108 may be structured to have a lower protruding portion (that is opposite the end adjacent to the vapor outlet of the mouthpiece structure 102) that is configured to engage with the concave end of the vaporizer 106. The cartridge 108 may be configured to unite with the vaporizer 106 via a friction-fit arrangement or a snap-fit arrangement, although example embodiments are not limited thereto. In addition, a coupling action may occur so that the vaporizer 106 can access (e.g., be in fluidic communication with) the pre-vapor formulation in the cartridge 108. The coupling action may occur simultaneously with or subsequent to the connection of the cartridge 108 to the vaporizer 106.

Access to the pre-vapor formulation in the cartridge 108 is restricted by a seal 110. The seal 110 may be in a form of a ball check valve arrangement. In such an instance, the vaporizer 106 may include an access member that is configured to press against a ball structure of the ball check valve arrangement to release the pre-vapor formulation within the cartridge 108 during the coupling action. The access member of the vaporizer 106 may draw the pre-vapor formulation (e.g., via capillary action) from the cartridge 108 into the vaporizer 106. Because the ball structure of the ball check valve arrangement is spring-biased, the ball structure will press against an inner surface of the outlet of the cartridge 108 to reseal the cartridge 108 when the cartridge 108 is detached from the vaporizer 106 (e.g., during replacement of the cartridge 108). In another example, the seal 110 may be an impermeable material that is designed to be pierced by the access member of the vaporizer 106 in order to access the pre-vapor formulation within the cartridge 108.

The coupling action may involve pressing the mouthpiece structure 102 against the dispensing body 104 to obtain the proper connection. In particular, the cartridge 108 may be pushed against the corresponding portion of the vaporizer 106 to establish the requisite fluidic communication therebetween. During the operation of the e-vapor device 100, air may enter via an inlet 114 and exit via an outlet 116. The vapor may be dispensed via the vapor passage 118. The force applied to achieve the coupling action may result in a temporary, longitudinal displacement of the vaporizer 106. The vaporizer 106 interacts with the ratchet assembly 112 in the dispensing body 104, and a spring may be arranged under the ratchet assembly 112. The ratchet assembly 112 may include a toothed structure and a pawl configured to engage the teeth of the toothed structure so as to permit only a one-way advancement (e.g., one direction of movement) of the toothed structure.

As noted above, the ratchet assembly 112 may be configured to undergo a mechanical incrementation with each coupling action between the cartridge 108 and the vaporizer 106. In particular, when a new cartridge 108 is loaded in the e-vapor device 100 by pushing the new cartridge 108 against the corresponding portion of the vaporizer 106 to perform the coupling action, the force from the pushing will additionally cause the vaporizer 106 and the ratchet assembly 112 to undergo a temporary, longitudinal displacement into the dispensing body 104 via the spring while also causing the ratchet assembly to mechanically advance. For example, the ratchet assembly 112 may be configured to rotate in response to the coupling action as part of the mechanical incrementation. With the mechanical incrementation, the ratchet assembly 112 is configured to initially engage and hold the vaporizer 106 and to subsequently release the vaporizer 106 for simultaneous removal with the cartridge 108 after a designated number of mechanical incrementations.

In an example embodiment, the ratchet assembly 112 may be configured to initially latch onto the vaporizer 106 during the coupling action and to incrementally disengage from the vaporizer 106 with each coupling action such that the vaporizer 106 is released from the ratchet assembly 112 after the designated number of coupling actions. In particular, the ratchet assembly 112 may include a rim structure that is configured to rotate and obstruct the guide structures on the outer side wall of the vaporizer 106 when the vaporizer 106 undergoes a temporary, longitudinal displacement into the dispensing body 104 during a coupling action. As a result, the cartridge 108, when spent, will be detached from the e-vapor device 100 without also removing the vaporizer 106. The rim structure of the ratchet assembly 112 may be configured to rotate with each coupling action (e.g., insertion of a new cartridge 108) until a notched section (or similar arrangement) is reached that corresponds to each guide structure of the vaporizer 106, which will allow the guides structures to pass through via the notched sections, thereby releasing the vaporizer 106 for removal with the cartridge 108. Accordingly, the vaporizer 106 can be discarded after utilization with a designated number of cartridges 108, thus reducing or preventing the overuse of the vaporizer 106 and the potentially unpleasant sensory effects associated therewith.

Alternatively, the ratchet assembly 112 may be configured to incrementally engage the vaporizer 106 to the cartridge 108 with each coupling action such that the vaporizer 106 is conjoined to the cartridge 108 after the designated number of coupling actions. In such an instance, the cartridge 108 may be fluidically connected to the vaporizer 106 during the coupling action without establishing a mechanical connection therebetween that would be sufficient to allow the cartridge 108 and the vaporizer 106 to be simultaneously removed. Instead, the ratchet assembly 112 can be configured to establish such a mechanical connection after a designated number of coupling actions.

Figure 5:
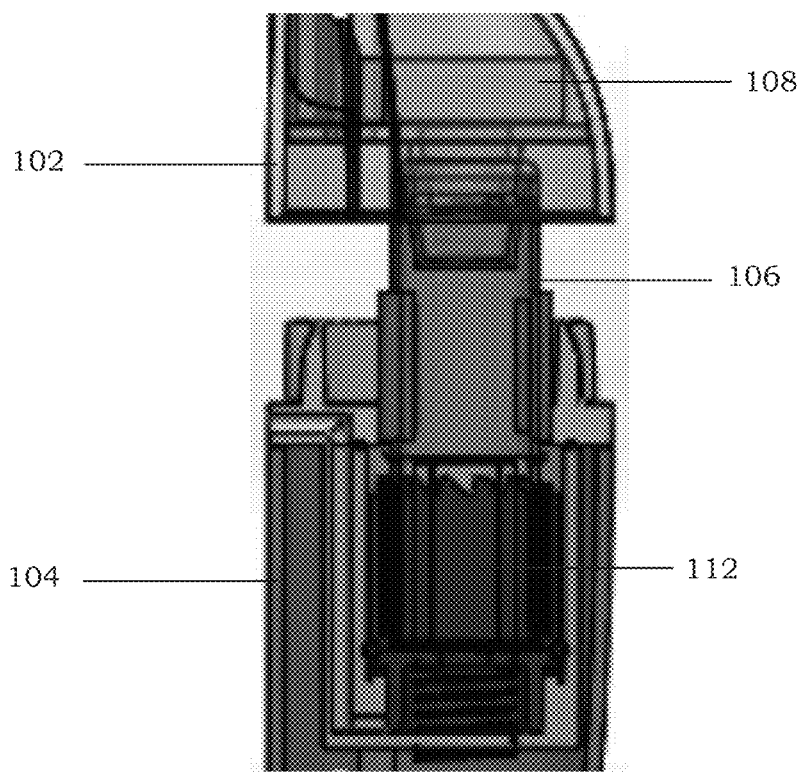
FIG. 5 is a partial, cross-sectional view of a simultaneous removal of the mouthpiece structure and vaporizer of the e-vapor device in FIG. 1.

FIG. 5 is a partial, cross-sectional view of a simultaneous removal of the mouthpiece structure and vaporizer of the e-vapor device in FIG. 1. Referring to FIG. 5, the ratchet assembly 112 may be configured to facilitate the simultaneous removal of the mouthpiece structure 102 with the vaporizer 106 coupled thereto after two to ten coupling actions (e.g., three to six coupling actions or four to five coupling actions). As a result, the cartridge 108 may be removed along with the mouthpiece structure 102 and at the same time as the vaporizer 106. In an example embodiment, each coupling action may correspond to the connection of a new cartridge 108 to the vaporizer 106. For instance, the e-vapor device 100 may be configured such that an adult vaper may replace the cartridge 108 three times (for every one time the vaporizer 106 is replaced), and upon depletion of the third replacement cartridge 108, the vaporizer 106 may be pulled out together with the depleted third replacement cartridge 108 and discarded. The frequency of replacement for the vaporizer 106 may depend on the pre-vapor formulation of the cartridge 108 and/or operating parameters of the e-vapor device 100. There is no particular limit on the number of cartridges 108 and vaporizers 106 that can be used during the life of the e-vapor device 100, since the total will depend on a variety of factors, including the vaping environment and handling habits of the adult vaper.

Figure 6:
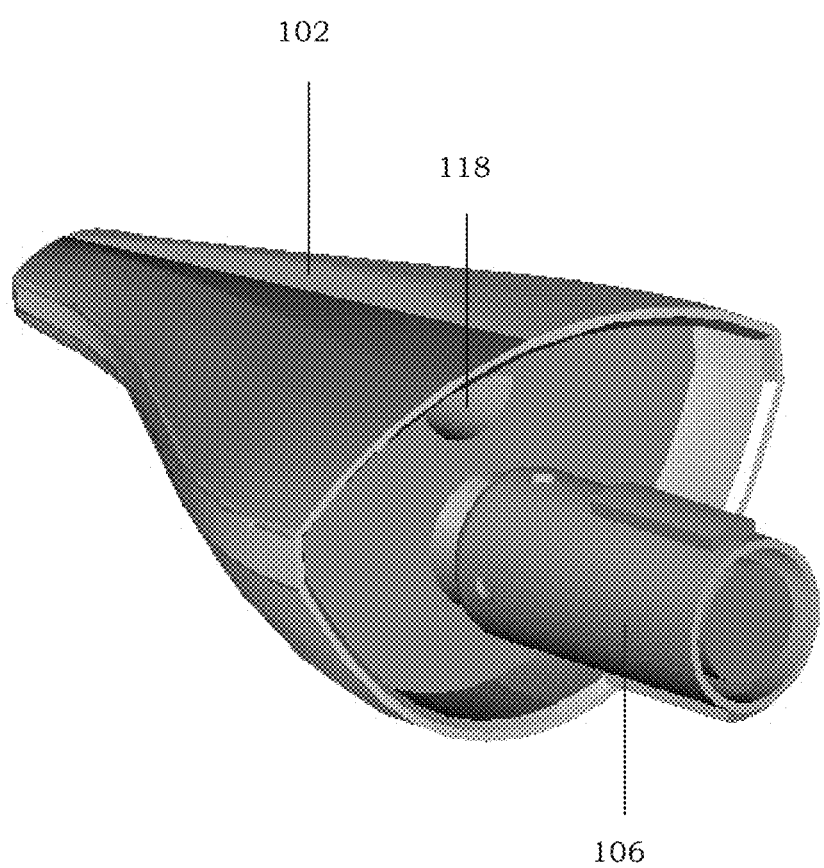
FIG. 6 is a perspective view of the mouthpiece structure and vaporizer that were simultaneously removed in FIG. 5.

FIG. 6 is a perspective view of the mouthpiece structure and vaporizer that were simultaneously removed in FIG. 5. Referring to FIG. 6, the mouthpiece structure 102 with the vaporizer 106 coupled thereto are intended to be discarded when detached from the dispensing body 104. As a result, the cartridge 108 (e.g., FIG. 5) within the mouthpiece structure 102 will be discarded as well. As discussed supra, the e-vapor device 100 is designed such that the vaporizer 106 will be removed after a certain number of cartridges 108 have been used. With such a design, an adult vaper does not need to consciously track the number of cartridges 108 used for purposes of determining when the vaporizer 106 should be replaced. Rather, the vaporizer 106 will be automatically removed with the cartridge 108 (and the mouthpiece structure 102 depending on the example embodiment) in accordance with the device design (e.g., replace the vaporizer together with the removal of the fourth or fifth cartridge). Otherwise, the vaporizer 106 will remain in the dispensing body 104 if the replacement time has not yet been reached in accordance with the device design. Consequently, the risk of overusing the vaporizer 106 (which can result in an undesirable taste) can be reduced or prevented.

Figure 7:
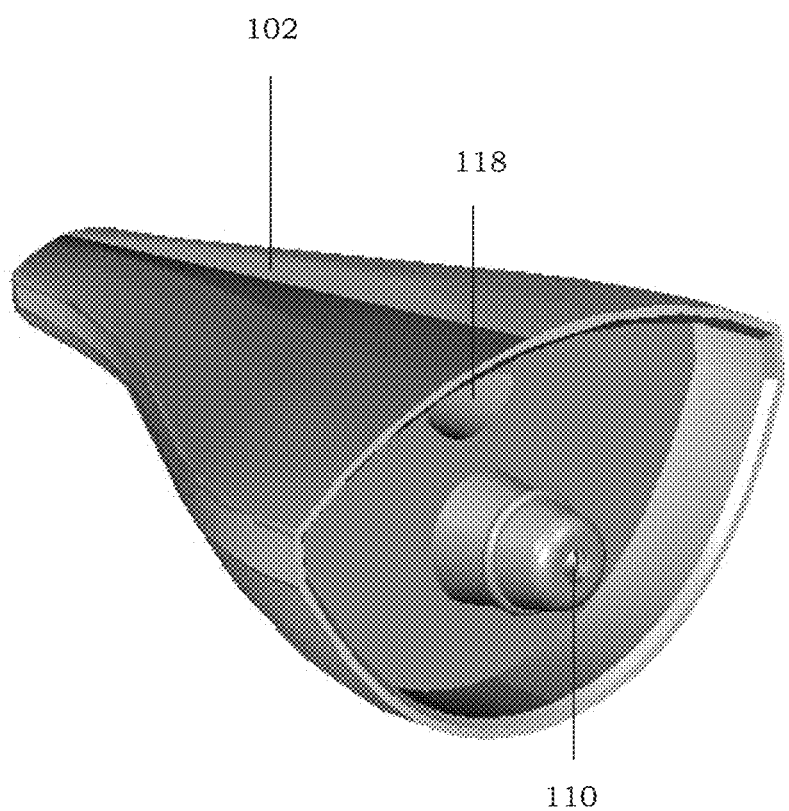
FIG. 7 is a perspective view of the mouthpiece structure in FIG. 6 without the vaporizer coupled thereto.

FIG. 7 is a perspective view of the mouthpiece structure in FIG. 6 without the vaporizer coupled thereto. Referring to FIG. 7, the mouthpiece structure 102 has a lower protruding portion that is configured to engage with the concave end of the vaporizer 106. The lower protruding portion is on an opposite end of the mouthpiece structure 102 from the vapor outlet. The vapor passage 118 extends through the mouthpiece structure 102 to the vapor outlet. Access to the pre-vapor formulation in the cartridge 108 (within the mouthpiece structure 102) is restricted by a seal 110. The seal 110 may be in a form of a ball check valve arrangement. For instance, such an arrangement may include a ball structure that is spring-biased such that the ball structure will press against an inner surface of the outlet at the lower protruding portion so as to seal the pre-vapor formulation within the cartridge 108. Because a spring-biased ball structure is used in this instance, the pre-vapor formulation can be readily resealed within the cartridge 108 when the cartridge 108 is detached from the vaporizer 106 (e.g., during replacement of the cartridge 108). In another example, the seal 110 may be an impermeable material that is designed to be pierced by the access member of the vaporizer 106 in order to access the pre-vapor formulation within the cartridge 108.

Figure 8:
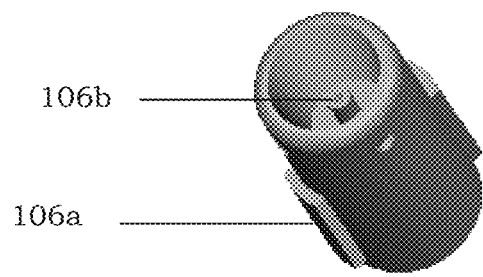
FIG. 8 is a perspective view of the vaporizer in FIG. 6 without the mouthpiece structure coupled thereto.

FIG. 8 is a perspective view of the vaporizer in FIG. 6 without the mouthpiece structure coupled thereto. Referring to FIG. 8, the vaporizer 106 may be cylindrically shaped with guide structures 106a on its outer side wall. Although the vaporizer is shown with two guide structures 106a, it should be understood that example embodiments are not limited thereto. As will be described in more detail below, the guide structures 106a may play a role in timing when the vaporizer 106 should be removed together with the cartridge 108 in the mouthpiece structure 102. In addition, the vaporizer 106 has a concave end with an access member 106b that is configured to interact with the seal 110 of the mouthpiece structure 102 to release the pre-vapor formulation within the cartridge 108 during the coupling action. The access member 106b of the vaporizer 106 may draw the pre-vapor formulation (e.g., via capillary action) from the cartridge 108 into the vaporizer 106. In a non-limiting embodiment, the access member 106b may be in the form of a relatively slender, tubular structure. When in the form of a tubular structure, the channel extending through the access member 106b may be sized appropriately to achieve the desired capillary effect. Furthermore, the channel may optionally include a wick to help draw or otherwise control the supply of pre-vapor formulation from the cartridge 108 to the vaporizer 106.

Figure 9:
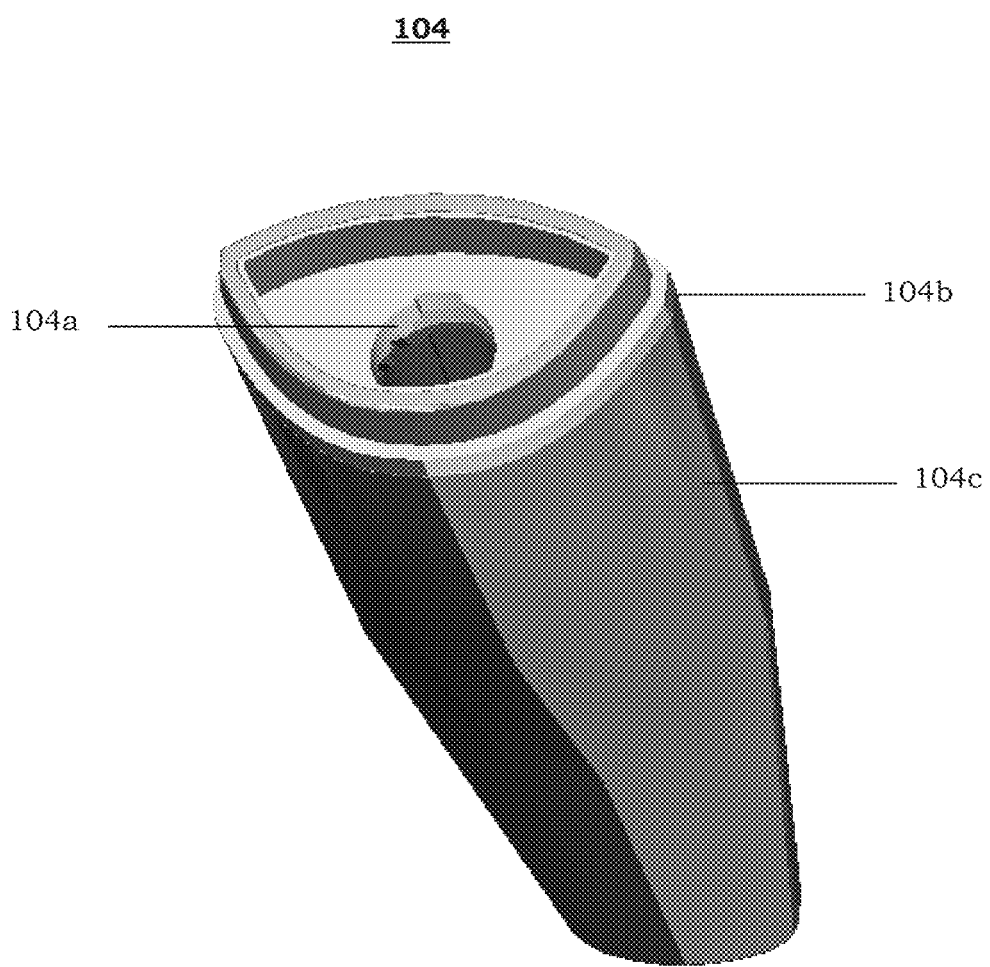
FIG. 9 is a perspective view of the dispensing body in FIG. 1 without the mouthpiece structure coupled thereto.

FIG. 9 is a perspective view of the dispensing body in FIG. 1 without the mouthpiece structure coupled thereto. Referring to FIG. 9, the dispensing body 104 includes a body section 104c, a body end plate 104b, and an opening 104a defined by the body end plate 104b. The opening 104a in the dispensing body 104 is designed to receive the vaporizer 106 and, thus, is shaped to correspond to a circumferential profile of the vaporizer 106. For instance, the opening 104a may be circular with two oppositely-arranged indentations. In such an instance, the circular shape of the opening 104a is designed to accommodate the cylindrical shape of the vaporizer 106, while the indentations are designed to accommodate the guide structures 106a of the vaporizer 106. Similarly, in an example embodiment, the ratchet assembly 112 within the dispensing body 104 defines a recess that accommodates the contours of the vaporizer 106. The recess defined by the ratchet assembly 112 may be a cylindrical cavity with two oppositely-arranged indentations and dimensioned similarly (e.g., similar aperture size) to the opening 104a defined by the body end plate 104b so as to facilitate the seating of the vaporizer 106.

Figure 10:
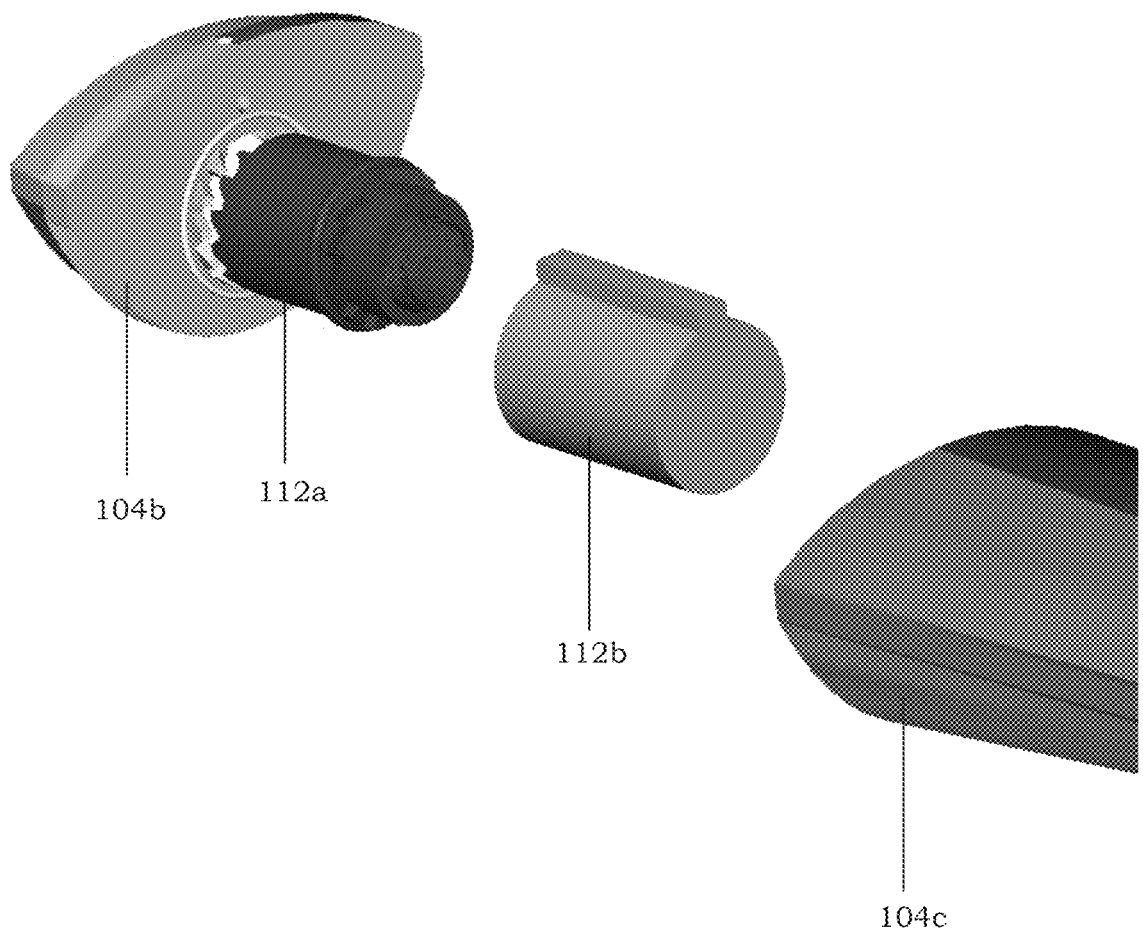
FIG. 10 is a partially exploded view of the dispensing body in FIG. 9.

FIG. 10 is a partially exploded view of the dispensing body in FIG. 9. Referring to FIG. 10, the ratchet assembly 112 includes an inner race 112a and an outer race 112b. When the dispensing body 104 is assembled, the inner race 112a is situated within the outer race 112b, and the ratchet assembly 112 is enclosed by the body end plate 104b and the body section 104c. The inner race 112a has a first set of teeth at an end adjacent to the body end plate 104b and a second set of teeth on a side surface of the inner race 112a. The first set of teeth of the inner race 112a is configured to engage with a set of teeth on the underside of the body end plate 104b. Although not shown in this view, the outer race 112b has an annular set of teeth on its inner sidewall. The second set of teeth of the inner race 112a is configured to engage the annular set of teeth within the outer race 112b. A spring is arranged between the inner race 112a and the outer race 112b to alternately engage the inner race 112a with the body end plate 104b and the outer race 112b. The operation of the ratchet assembly 112 will be discussed in further detail below.

Figure 11:
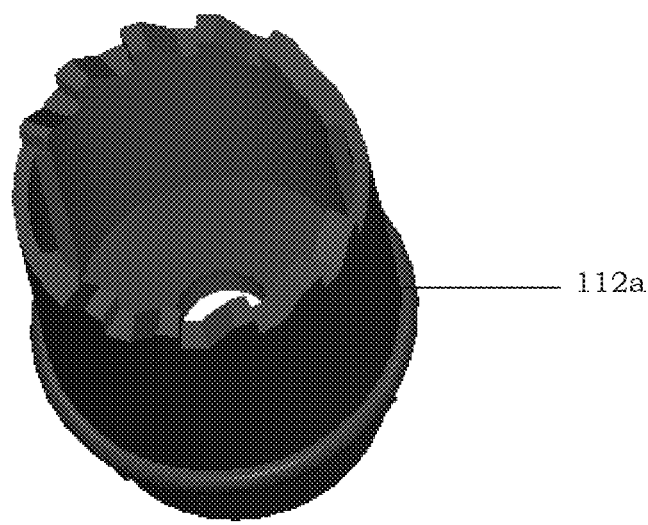
FIG. 11 is an enlarged view of the ratchet assembly in FIG. 10.
Figure 11:
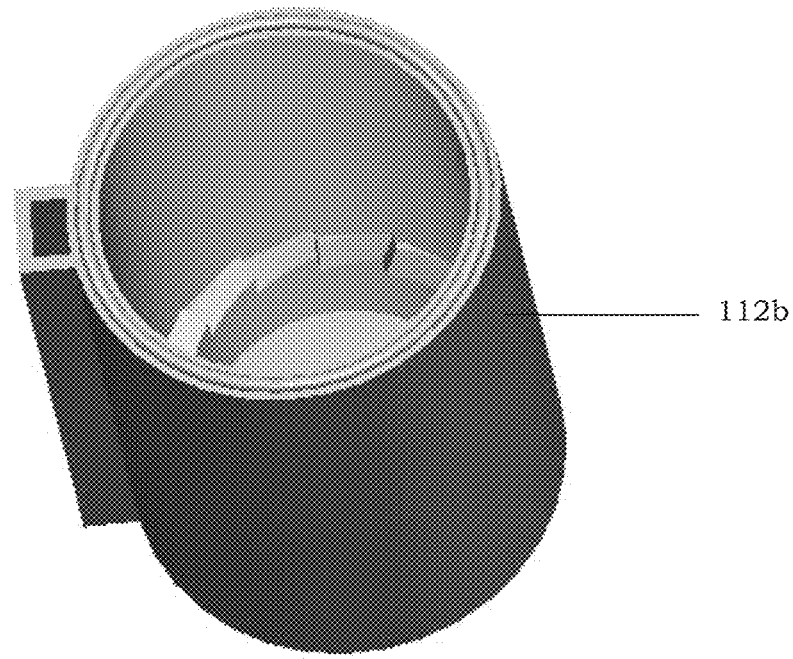

FIG. 11 is an enlarged view of the ratchet assembly in FIG. 10. Referring to FIG. 11, the inner race 112a of the ratchet assembly 112 has oppositely-arranged indentations on its inner sidewall. The oppositely-arranged indentations of the inner race 112a are configured to accommodate the guide structures 106a of the vaporizer 106. The first set of teeth of the inner race 112a may be arranged around the rim of the inner race 112a other than at the portions corresponding to the indentations. The outer race 112b has an annular set of teeth on its inner sidewall. The outer race 112b may also be rendered stationary (e.g., so as to not rotate or otherwise move) within the dispensing body 104. As discussed in connection with FIG. 10, a spring will be arranged between the inner race 112a and the outer race 112b.

When a vaporizer 106 is loaded in the opening 104a of the dispensing body 104 and initially seated in the inner race 112a, the vaporizer 106 will come to rest at a neutral position based on the underlying spring, which is in an uncompressed state. Next, when a mouthpiece structure 102 is connected to the dispensing body 104, the lower protruding portion of the mouthpiece structure 102 will engage with the vaporizer 106 while also pushing the vaporizer 106 and consequently the inner race 112a so as to overcome the resilient nature of the spring and transition the spring to a compressed state. As a result, the second set of teeth of the inner race 112a will engage with the annular set of teeth within the outer race 112b. The second set of teeth of the inner race 112a may be offset relative to the annular set of teeth within the outer race 112b. In addition, because the second set of teeth of the inner race 112a and the annular set of teeth within the outer race 112b are angled, the mating of the teeth will cause the inner race 112a (and the vaporizer 106 seated therein) to rotate. The combination of the vaporizer 106 being pushed into the dispensing body 104 and rotated will result in the guide structures 106a of the vaporizer 106 being underneath the body end plate 104b (and, thus, no longer aligned with the corresponding indentations of the opening 104a).

Consequently, when the mouthpiece structure 102 is disconnected from the dispensing body 104 (e.g., to replace a depleted cartridge 108), the mouthpiece structure 102 can be disengaged without the vaporizer 106 being removed at the same time. In the absence of the mouthpiece structure 102, the spring will decompress and cause the first set of teeth of the inner race 112a to engage with the set of teeth on the underside of the body end plate 104b. When the mouthpiece structure 102 (e.g., new mouthpiece structure 102 with a full cartridge 108) is subsequently connected to the dispensing body 104, the cycle repeats and the vaporizer 106 will be pushed inward and rotated via the inner race 112a. In this manner, the vaporizer 106 can be rotated in increments with the changing of the mouthpiece structure 102 until the guide structures 106a of the vaporizer 106 become aligned with the corresponding indentations of the opening 104a so as to release the vaporizer 106 for simultaneous removal during the replacement of the mouthpiece structure 102. Such a design ensures that the vaporizer 106 will be replaced regularly (e.g., every five cartridges 108) without requiring an additional conscious effort from an adult vaper, thereby enhancing the vaping experience. It should be understood that the ratchet assembly 112 can be modified as needed in accordance with the teachings herein in order to achieve the predetermined or desired timing/frequency for replacing the vaporizer 106.

Figure 12:
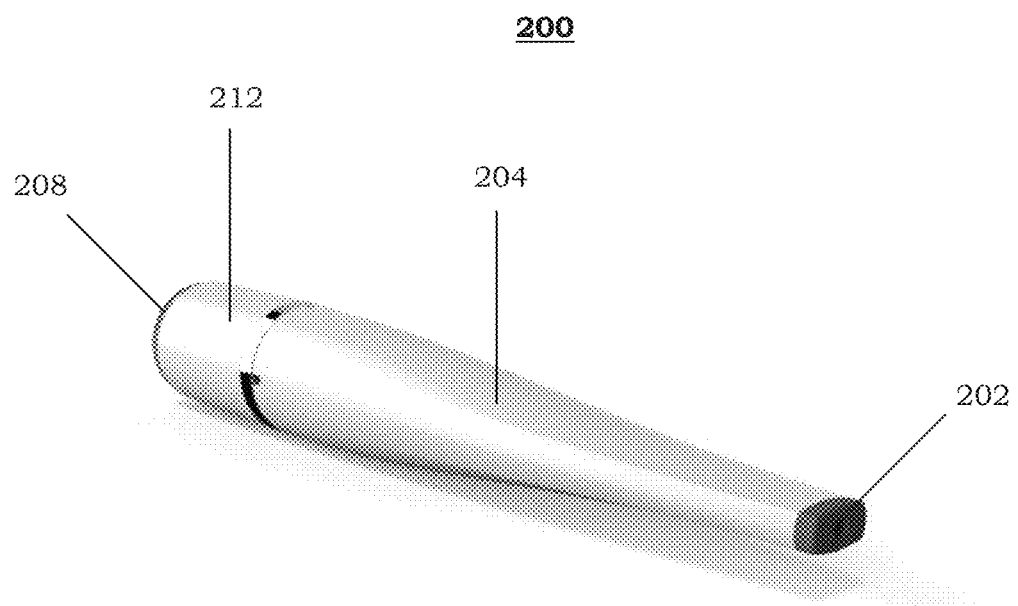
FIG. 12 is a perspective view of an e-vapor device with a cartridge-in-base configuration according to an example embodiment.

FIG. 12 is a perspective view of an e-vapor device with a cartridge-in-base configuration according to an example embodiment. Referring to FIG. 12, the e-vapor device 200 includes a base structure 212 that is connected to a dispensing body 204. The dispensing body 204 includes a mouthpiece end with a mouthpiece structure 202 and a vaporizer at an opposing base end. The base end is configured to couple with a cartridge 208 such that a pre-vapor formulation is in fluidic communication with the vaporizer. The cartridge 208 is configured to hold the pre-vapor formulation therein. The cartridge 208 may be a sealed container. The vaporizer is configured to heat the pre-vapor formulation to generate a vapor.

Figure 13:
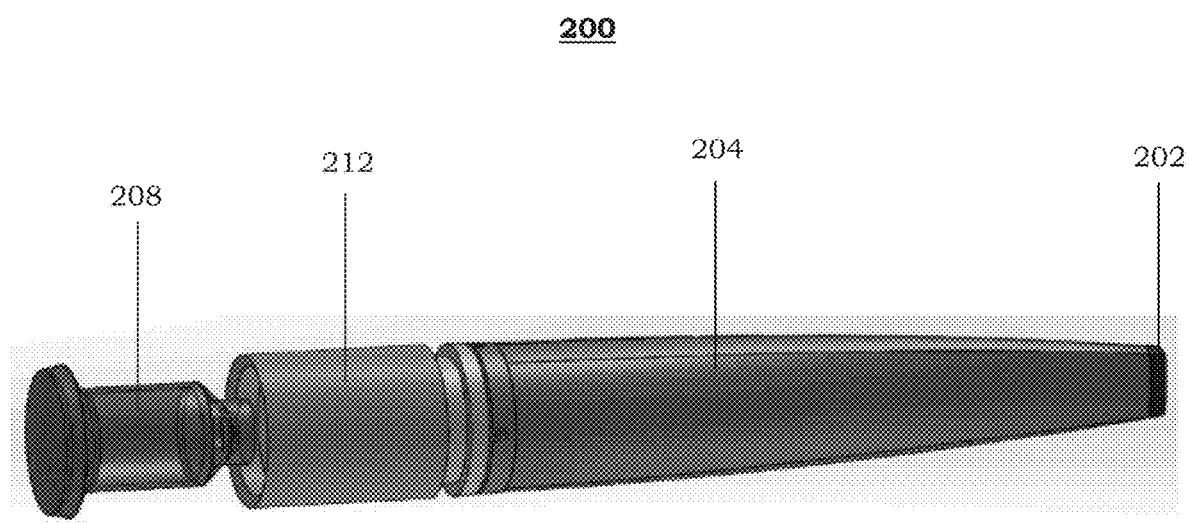
FIG. 13 is a partially exploded view of the e-vapor device in FIG. 12.

FIG. 13 is a partially exploded view of the e-vapor device in FIG. 12. Referring to FIG. 13, the dispensing body 204 may taper toward the mouthpiece structure 202. The base structure 212 may be attached to the dispensing body 204 via a threaded arrangement, although example embodiments are not limited thereto. The cartridge 208 is configured for insertion into the base structure 212 and may be secured via a number of suitable arrangements.

Figure 14:
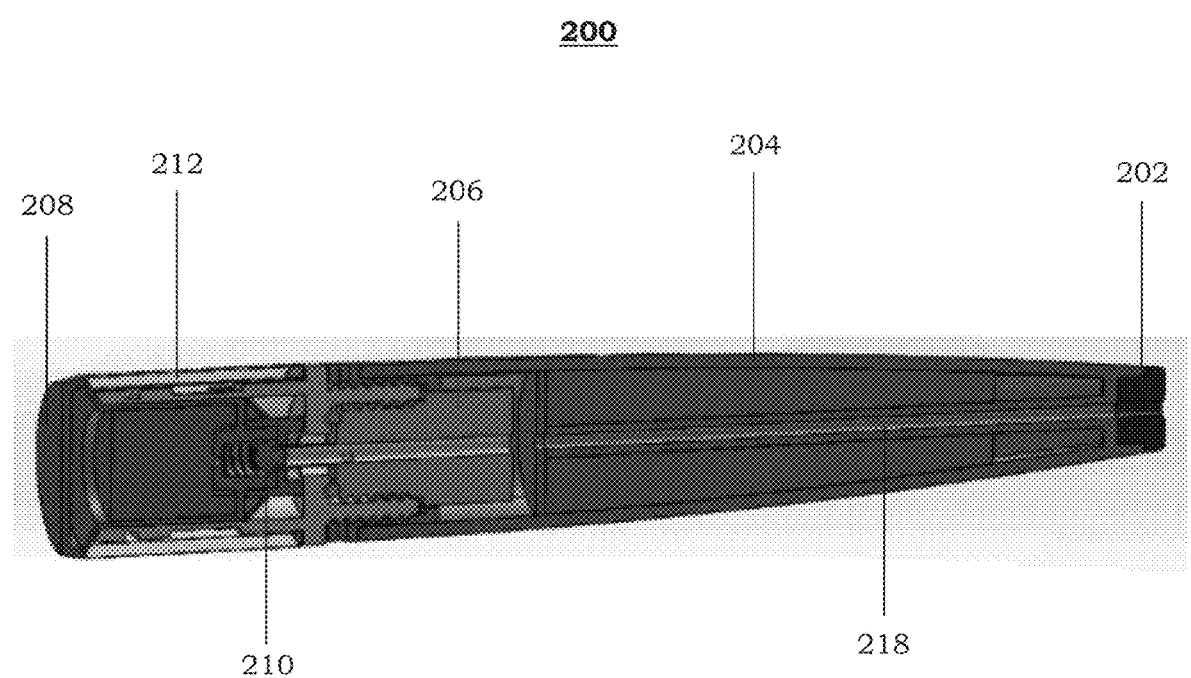
FIG. 14 is a cross-sectional view of the e-vapor device in FIG. 12.

FIG. 14 is a cross-sectional view of the e-vapor device in FIG. 12. Referring to FIG. 14, access to the pre-vapor formulation in the cartridge 208 may be restricted with a seal 210. The seal 210 may be a ball check valve arrangement, although example embodiments are not limited thereto. The vaporizer 206 is arranged within the base end of the dispensing body 204. A vapor passage 218 extends within the dispensing body 204 from the vaporizer 206 to the mouthpiece structure 202. The dispensing body 204 may further include a battery between the mouthpiece structure 202 at the mouthpiece end and the vaporizer 206 at the opposing base end.

Figure 15:
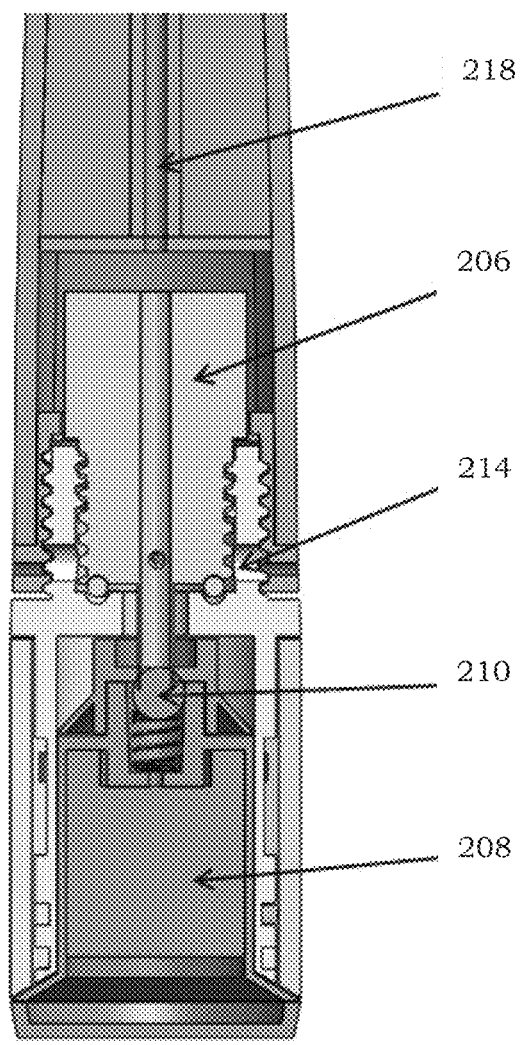
FIG. 15 is a partial, cross-sectional view of the e-vapor device in FIG. 12.

FIG. 15 is a partial, cross-sectional view of the e-vapor device in FIG. 12. Referring to FIG. 15, the ball structure of the ball check valve arrangement of the seal 210 is pushed inward when the cartridge 208 is coupled to the vaporizer 206, thereby allowing the pre-vapor formulation in the cartridge 208 to be in fluidic communication with the vaporizer 206. Air may flow into the vaporizer 206 via an inlet 214. The vapor generated by the vaporizer 206 is directed through the vapor passage 218 to the mouthpiece structure 202.

Figure 16:
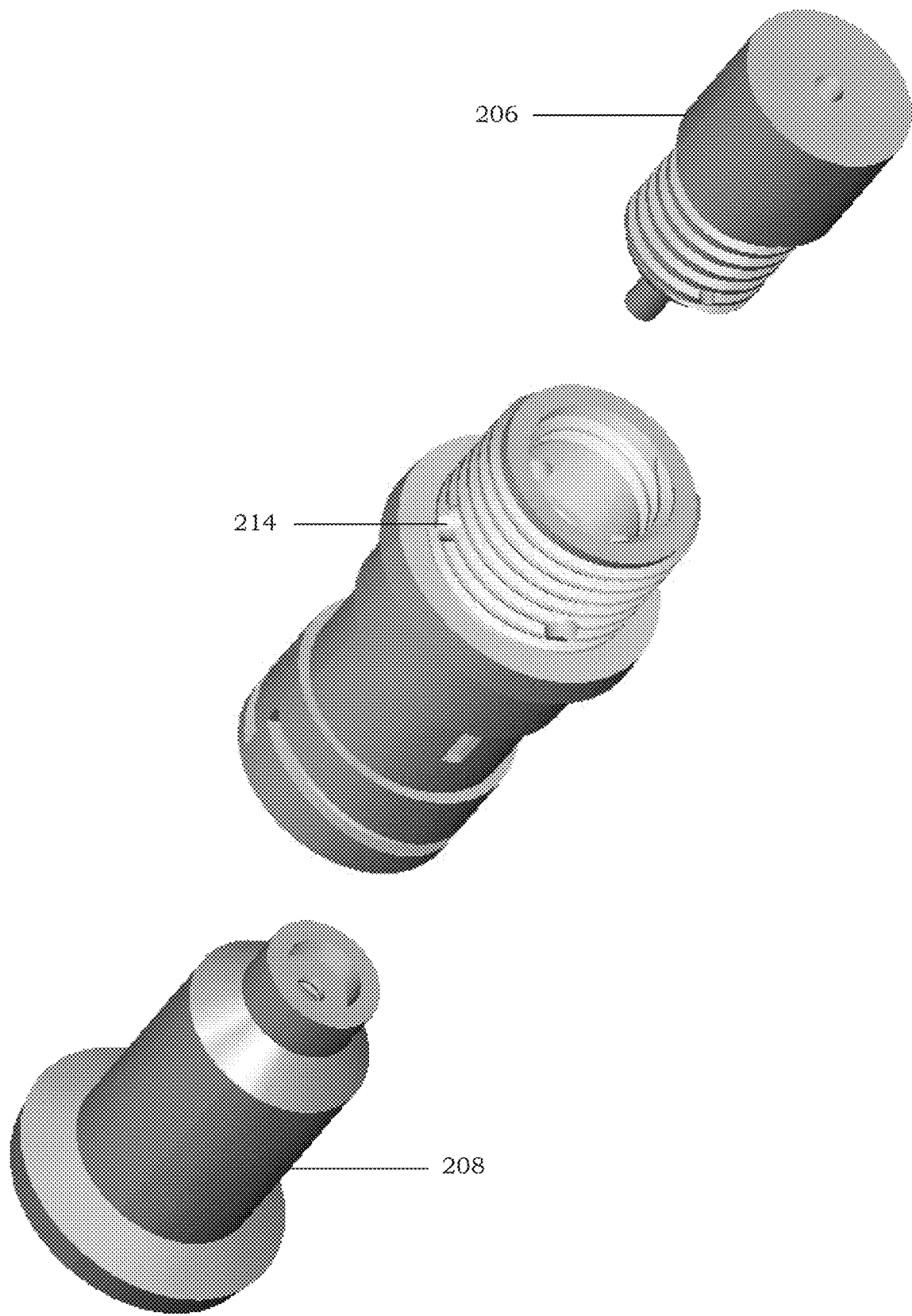
FIG. 16 is a perspective view of the cartridge, inner collar, and vaporizer in FIG. 15.

FIG. 16 is a perspective view of the cartridge, inner collar, and vaporizer in FIG. 15. Referring to FIG. 16, the cartridge 208 is configured to engage the inner collar at one end, while the vaporizer 206 is configured to engage the inner collar at an opposing end. When assembled, the cartridge 208 will be coupled to the vaporizer 206 (within the inner collar), thereby allowing the pre-vapor formulation in the cartridge 208 to be in fluidic communication with the vaporizer 206. A plurality of inlets 214 for air may extend through a threaded portion of the inner collar, although example embodiments are not limited thereto.

Figure 17:
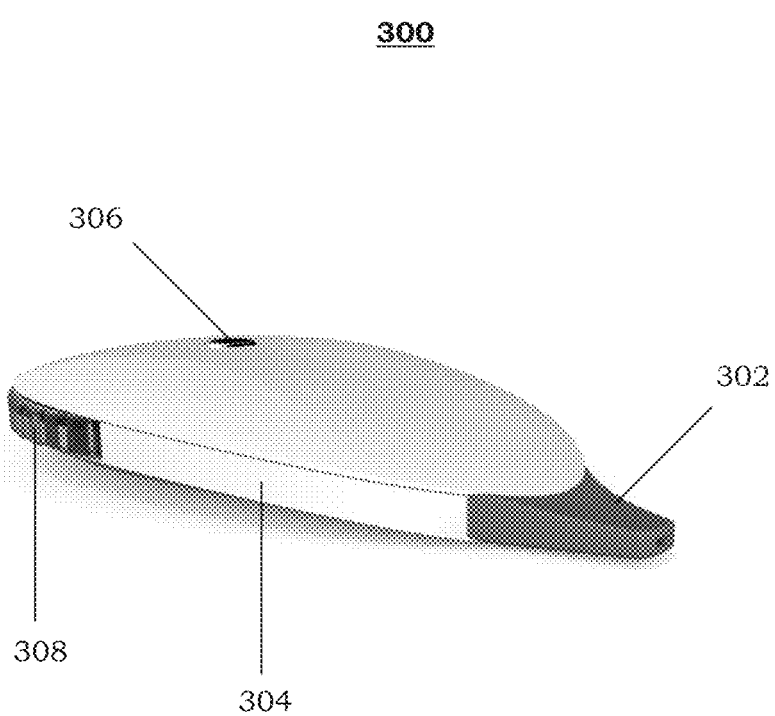
FIG. 17 is a perspective view of an e-vapor device with a disk cartridge configuration according to an example embodiment.

FIG. 17 is a perspective view of an e-vapor device with a disk cartridge configuration according to an example embodiment. Referring to FIG. 17, the e-vapor device 300 includes a dispensing body 304 having a disk-like or egg-like shape. However, other suitable shapes (e.g., elliptical shape) may also be suitable. The mouthpiece structure 302 is connected to a side surface of the dispensing body 304. The vaporizer 306 is visible through a top surface of the dispensing body 304.

Figure 18:
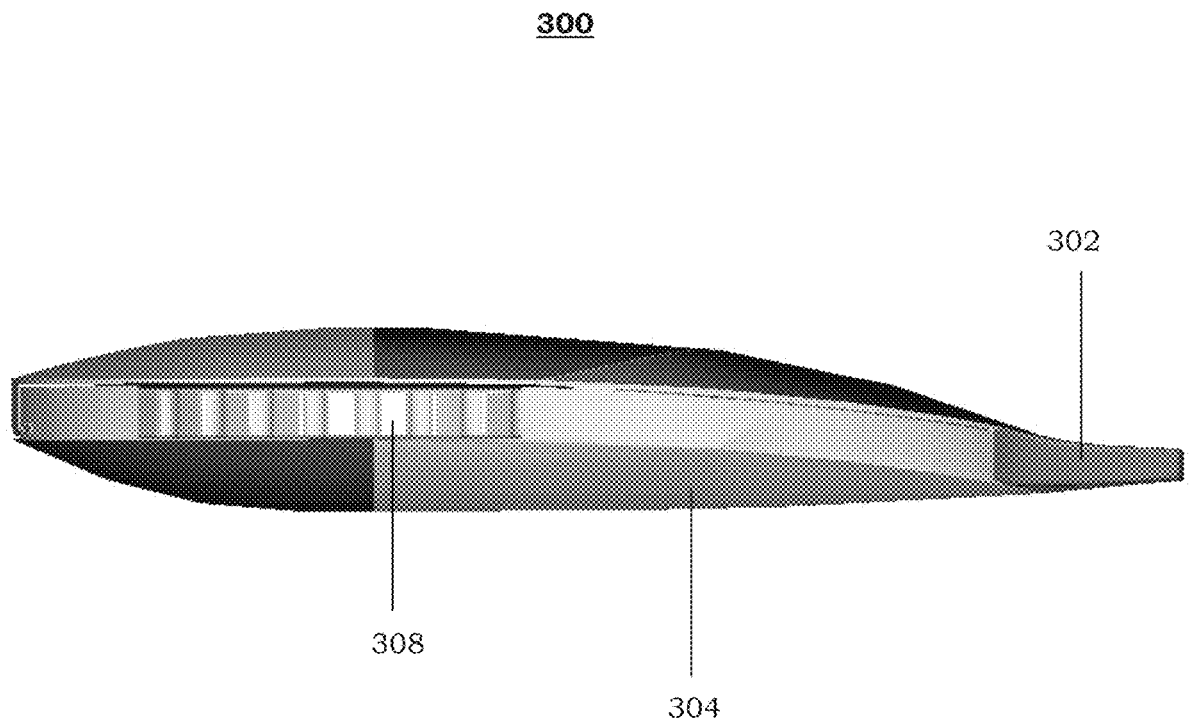
FIG. 18 is a side view of the e-vapor device in FIG. 17.

FIG. 18 is a side view of the e-vapor device in FIG. 17. Referring to FIG. 18, the e-vapor device 300 has a length that is greater than its height. The edges of the e-vapor device 300 may also be tapered to provide a more sleek appearance, although example embodiments are not limited thereto. A portion of the cartridge 308 is exposed through the dispensing body 304 to permit handling by an adult vaper (e.g., rotating the cartridge 308 to access the various compartments of pre-vapor formulation within).

Figure 19:
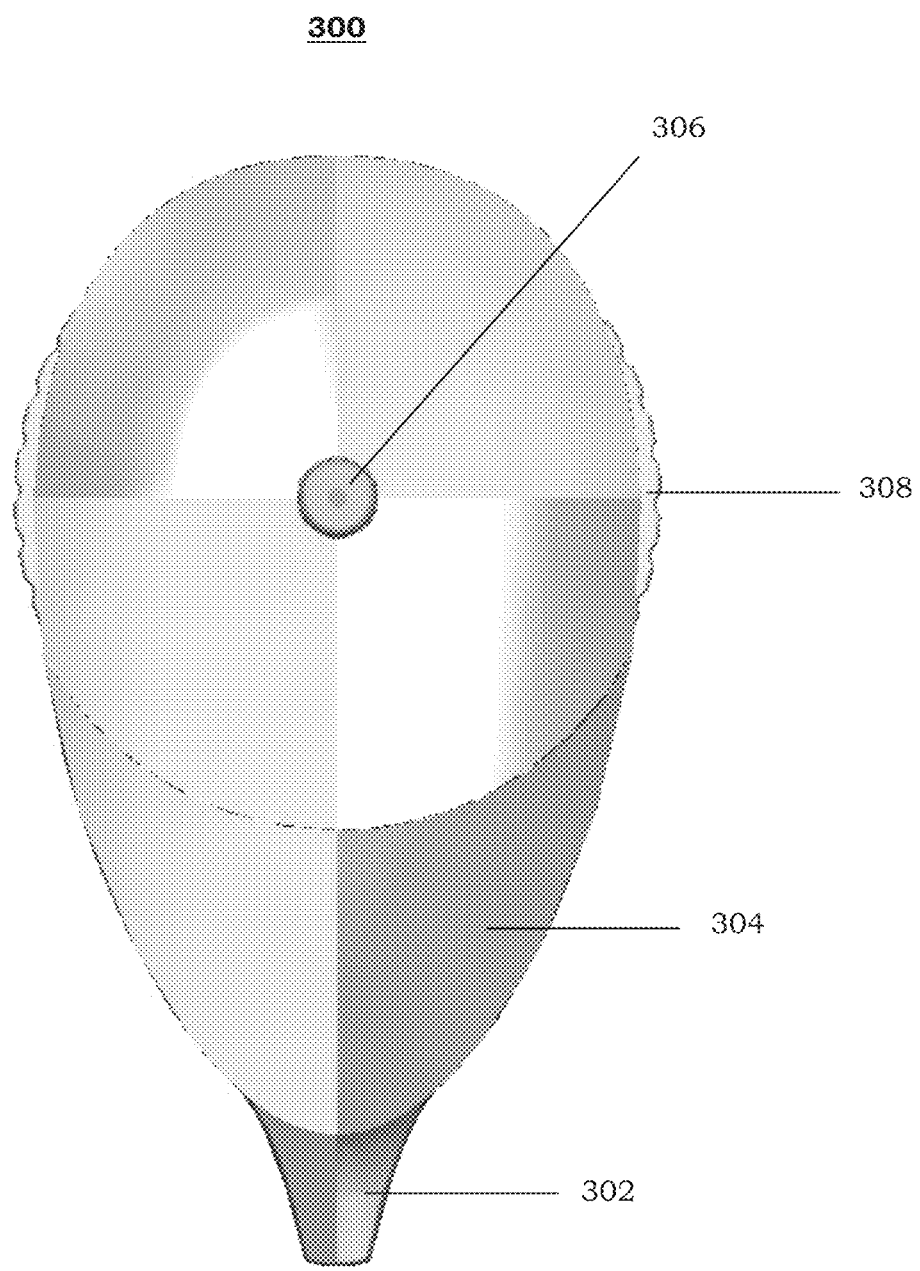
FIG. 19 is a top view of the e-vapor device in FIG. 17.

FIG. 19 is a top view of the e-vapor device in FIG. 17. Referring to FIG. 19, the e-vapor device 300 has a length that is greater than its width. The cartridge 308 (the edges of which are partially exposed) is configured to rotate around the vaporizer 306. The cartridge 308 may be provided with ridged side surface to enhance the ease of handling by an adult vaper.

Figure 20:
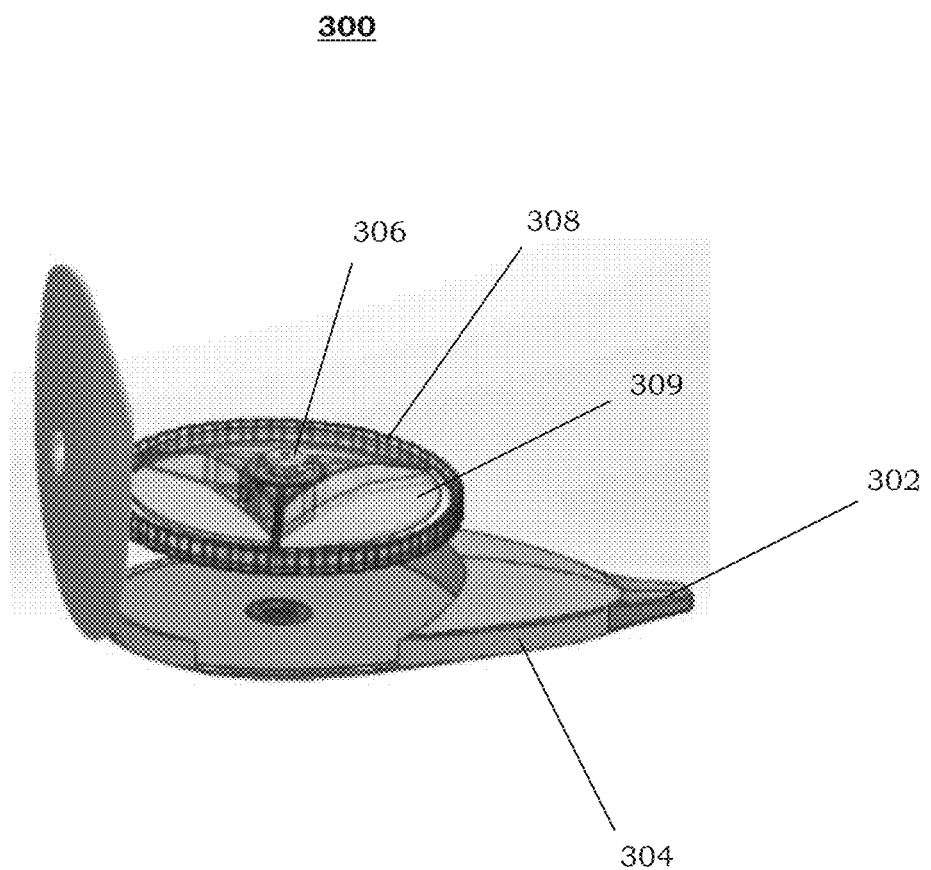
FIG. 20 is a partially exploded view of the e-vapor device in FIG. 17.

FIG. 20 is a partially exploded view of the e-vapor device in FIG. 17. Referring to FIG. 20, the dispensing body 304 includes a pivotable lid structure that is configured to open/close to receive (or remove) a cartridge 308 having a disk shape. The cartridge 308 includes a plurality of compartments 309. Although three compartments 309 are shown in FIG. 20, it should be understood that example embodiments are not limited thereto. For instance, the cartridge 308 may include two, four, or more compartments 309. Each of the plurality of compartments 309 is configured to hold a pre-vapor formulation therein. In addition, the plurality of compartments 309 are fluidically-isolated from each other. As a result, each compartment 309 of the cartridge 308 may hold a pre-vapor formulation of a different flavor and/or composition.

The vaporizer 306 may be structured to be a part of the dispensing body 304 or the cartridge 308. When the vaporizer 306 is structured to be a part of the dispensing body 304, the cartridge 308 may be structured to have an opening that is configured to engage the vaporizer 306. On the other hand, when the vaporizer 306 is structured to be a part of the cartridge 308, the dispensing body 304 may be configured to allow an engagement with the vaporizer 306. The cartridge 308 may be rotatably-mounted on the dispensing body 304 via the vaporizer 306. The cartridge 308 is configured to rotate around the vaporizer 306 such that one of the plurality of compartments 309 is aligned so as to be in fluidic communication with the vaporizer 306.

Figure 21:
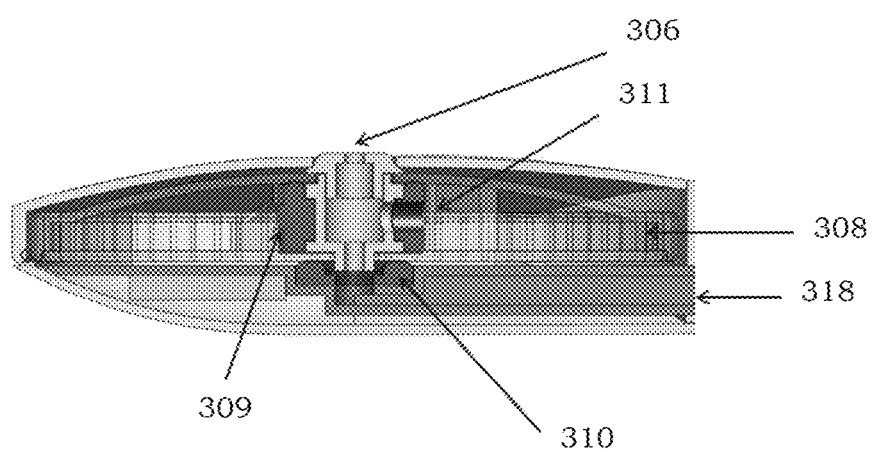
FIG. 21 is a partial, cross-sectional view of the e-vapor device in FIG. 17.

FIG. 21 is a partial, cross-sectional view of the e-vapor device in FIG. 17. Referring to FIG. 21, the vaporizer 306 is configured to remain stationary during a rotation of the cartridge 308. The feed passage 311 is configured to supply a pre-vapor formulation from the cartridge 308 to the vaporizer 306. Each of the plurality of compartments 309 includes a feed outlet that is configured to align with the feed inlet of the vaporizer 306 (upon rotation of the cartridge 308) to form the feed passage 311. Various arrangements may be used to help ensure a proper alignment of the feed passage 311 (e.g., mating member/recess type arrangements, magnetic arrangements). A seal 310 may be provided between vaporizer 306 and the vapor passage 318. During an operation of the e-vapor device 300, air may enter the vaporizer 306 from an opening in its top surface. The vapor generated by the vaporizer 306 is directed through the vapor passage 318 to the mouthpiece structure 302.

Figure 22:
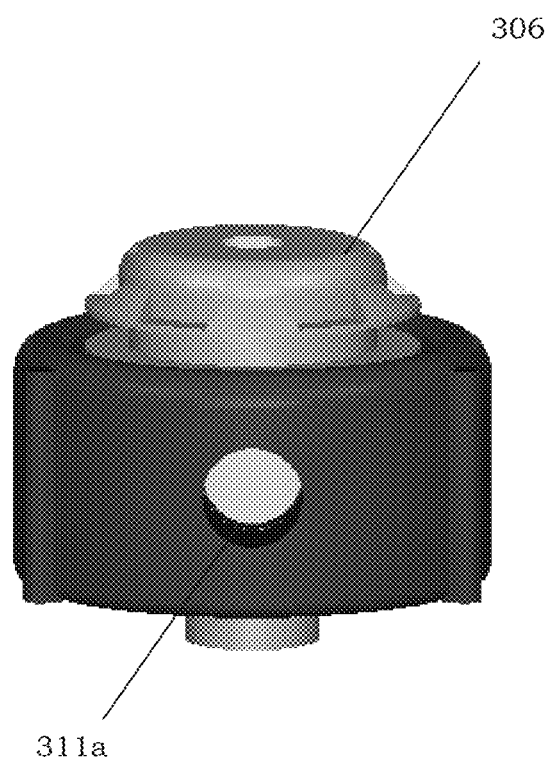
FIG. 22 is an enlarged view of the vaporizer in FIG. 17.

FIG. 22 is an enlarged view of the vaporizer in FIG. 17. Referring to FIG. 22, the vaporizer 306 has a feed inlet 311a that is configured to align with a feed outlet 311b of the cartridge 308 to form the feed passage 311 for supplying pre-vapor formulation from the cartridge 308 to the vaporizer 306. The vaporizer 306 is configured to heat the pre-vapor formulation to generate a vapor.

Figure 23:
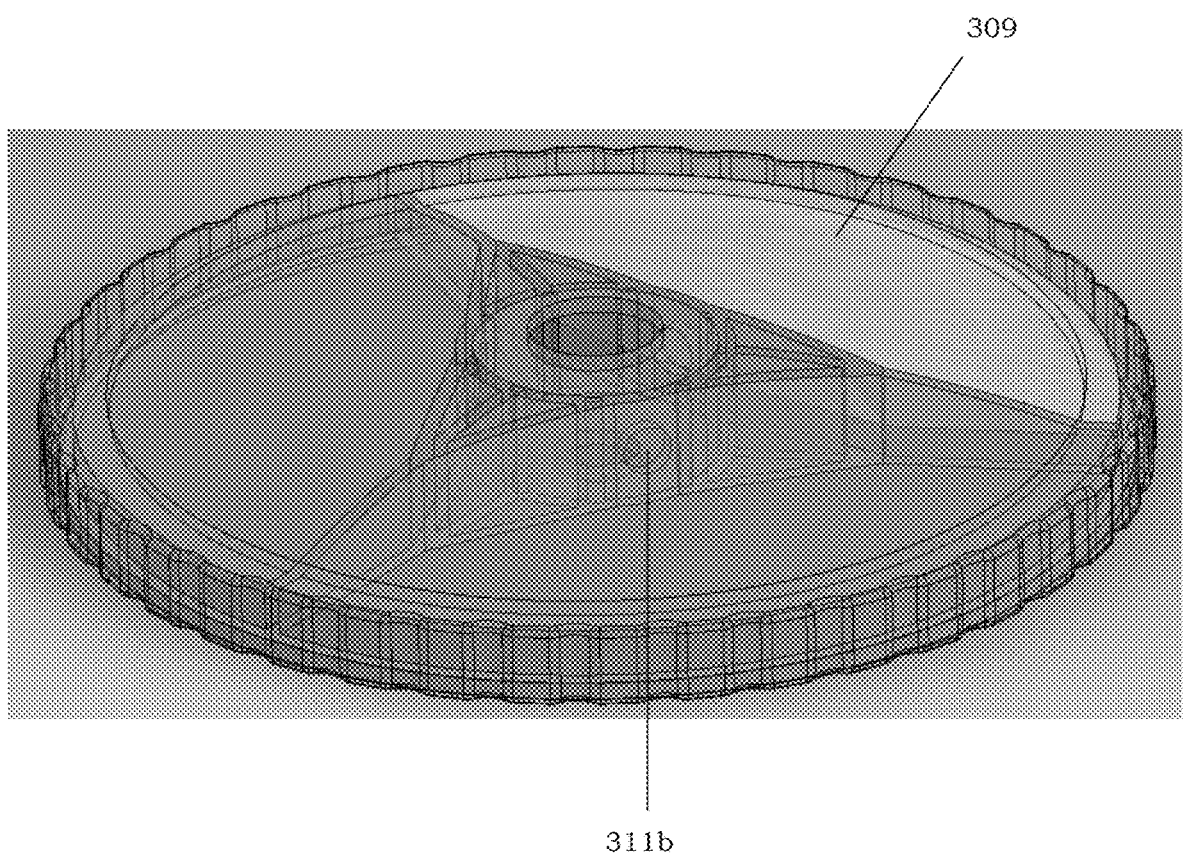
FIG. 23 is an enlarged view of the cartridge in FIG. 17.

FIG. 23 is an enlarged view of the cartridge in FIG. 17. Referring to FIG. 23, the cartridge 308 includes a plurality of compartments 309 configured to hold pre-vapor formulation. The pre-vapor formulation held in the plurality of compartments 309 may be of the same type or of a different type (e.g., different flavor, smell, color, strength, and/or base ingredient). Each of the plurality of compartments 309 has a feed outlet 311b that is configured to align with the feed inlet 311a of the vaporizer 306 to form the feed passage 311 for supplying pre-vapor formulation from the cartridge 308 to the vaporizer 306.

The e-vapor devices disclosed herein may be provided with memory devices and the associated circuitry so as to allow the receipt, storage, and transmission of information to/from other electronic devices. The smart capability, connecting features, and other related aspects of the mouthpiece structure, cartridge, dispensing body, and overall e-vapor device are additionally discussed in U.S. Application No. 62/151,148, U.S. Application No. 62/151,160, and U.S. Application No. 62/151,179, the entire contents of each of which are incorporated herein by reference.

Furthermore, the control circuitry may include a heater activation light that is configured to glow when the heater structure (of the vaporizer) is activated. The heater activation light may include an LED and may be arranged at an upstream end of the e-vapor device (distal end relative to an adult vaper) so that the heater activation light takes on the appearance of a burning coal during the application of negative pressure. Alternatively, the heater activation light may be arranged on the side of the e-vapor device so as to be more visible to the adult vaper and/or to provide a desired aesthetic appeal. The heater activation light may have various shapes, sizes, quantities, and configurations. For instance, the heater activation light may have a circular, elliptical, or polygonal shape (for one or more such lights). In another instance, the heater activation light may have a linear or annular form that is continuous or segmented. For example, the heater activation light may be provided as an elongated strip that extends along the body of the e-vapor device. In another example, the heater activation light may be provided as a ring that extends around the body of the e-vapor device. The ring may be in the first section (e.g., cartridge section) or the second section (e.g., battery section) of the e-vapor device. It should be understood that the heater activation light can be arranged on the end(s) and/or the sides of the e-vapor device. Moreover, the heater activation light can be utilized for e-vapor system diagnostics. The heater activation light can also be configured such that an adult vaper can activate and/or deactivate the heater activation light for privacy, such that, if desired, the heater activation light will not activate during vaping.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An e-vapor device comprising:
a cartridge including a plurality of compartments, each of the plurality of compartments configured to hold a pre-vapor formulation therein; and
a dispensing body including a vaporizer, the cartridge configured to be rotatably-mounted within the dispensing body via the vaporizer, the cartridge configured to rotate around the vaporizer such that one of the plurality of compartments is aligned so as to be in fluidic communication with the vaporizer, and the dispensing body is configured to expose a portion of the cartridge to permit a manual rotation of the cartridge.

2. The e-vapor device of claim 1, wherein the cartridge is disk-shaped.

3. The e-vapor device of claim 1, wherein the cartridge has a ridged side surface.

4. The e-vapor device of claim 1, wherein the plurality of compartments of the cartridge are fluidically-isolated from each other.

5. The e-vapor device of claim 1, wherein the vaporizer is configured to remain stationary during a rotation of the cartridge.

6. The e-vapor device of claim 1, wherein the vaporizer is visible through a top surface of the dispensing body.

7. The e-vapor device of claim 1, wherein the vaporizer defines a feed inlet configured to receive the pre-vapor formulation, and each of the plurality of compartments defines a feed outlet configured to release the pre-vapor formulation.

8. The e-vapor device of claim 7, wherein an alignment of the feed inlet and the feed outlet results in a feed passage for supplying the pre-vapor formulation from the cartridge to the vaporizer.

9. The e-vapor device of claim 1, wherein the dispensing body further includes a pivotable lid configured to open and close to permit an insertion or removal of the cartridge.

* * * * *